US00PP23086P2

(12) United States Plant Patent
Korlipara

(10) Patent No.: US PP23,086 P2
(45) Date of Patent: Sep. 25, 2012

(54) ***ECHINACEA* PLANT NAMED 'DAYDREAM'**

(50) Latin Name: ***Echinacea* spp.**
Varietal Denomination: Daydream

(75) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 44 days.

(21) Appl. No.: 13/066,142

(22) Filed: Apr. 6, 2011

(51) Int. Cl.
*A01H 5/00* (2006.01)

(52) U.S. Cl. ..... Plt./428

(58) Field of Classification Search ..... Plt./428
See application file for complete search history.

*Primary Examiner* — Susan McCormick Ewoldt
(74) *Attorney, Agent, or Firm* — Klarquist Sparkman, LLP

(57) ABSTRACT

A new and distinct *Echinacea* plant named 'Daydream' characterized by large butter yellow inflorescences, a medium habit with good branching, numerous strong stems, and excellent vigor.

1 Drawing Sheet

Botanical denomination: *Echinacea* spp.
Variety designation: 'Daydream'.

BACKGROUND OF THE INVENTION

The present invention relates to a new and distinct cultivar of *Echinacea* and given the cultivar name 'Daydream'. *Echinacea* is in the family Asteraceae. This new cultivar is a third generation seeding originating from a planned breeding program using *Echinacea paradoxa* as the seed parent in the original cross and *Echinacea purpurea* 'Ruby Giant' (an unpatented plant) as the pollen parent. The exact parents of this selection are unknown, unnamed, proprietary plants.

Compared to *Echinacea* 'Mac 'n' Cheese' (U.S. Plant Pat. No. 19,464), the most similar plant on the market, the new variety is more vigorous, has more crowns, larger inflorescences, and yellow rather than yellow orange flowers.

This new *Echinacea* cultivar is distinguished by:

1. large butter yellow inflorescences,
2. a medium habit with good branching,
3. numerous, strong stems, and
4. excellent vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

The photograph shows the inflorescences and habit of *Echinacea* 'Daydream' at 9 months old in the field in full sun in early July in Canby, Oreg.

DETAILED PLANT DESCRIPTION

The following is a detailed description of the new *Echinacea* cultivar based on observations of 18 month-old specimens growing in the garden in full sun in Canby, Oreg. Canby is in Zone 8 on the USDA Hardiness map. Temperatures range from a high of 95 degrees F. in August to an average of 32 degrees F. in January. Normal rainfall in Canby is 42.8 inches per year in the trial fields in Canby, Oreg. The color descriptions are all based on The Royal Horticultural Society Colour Chart, $5^{th}$ edition.

Plant:

*Type*.—Herbaceous perennial.
*Hardiness*.—USDA Zones 4 to 9.
*Size*.—Grows to about 54 cm wide and 65 cm tall to top of inflorescences.
*Form*.—Basal clump, with about 15 stems from the base.
*Vigor*.—Excellent.
*Roots*.—Fibrous, with many downward growing and few laterals, ivory in color, Yellow White 158D, roots develop easily from cuttings from the crown.

Stem (flowering):

*Type*.—Ascending, with 1 to 3 flowers per stem.
*Size*.—To 63 cm tall to a terminal inflorescence and 8 mm wide at base.
*Internode length*.—1 cm to 9 cm.
*Surface texture*.—Strigose.
*Color*.—Yellow Green N144A.

Leaf (basal):

*Type*.—Simple.
*Shape*.—Lanceolate.
*Arrangement*.—Basal.
*Blade size*.—Grows to 16 cm long and 5.5 cm wide.
*Margins*.—Sparsely serrate.
*Apex*.—Acute.
*Base*.—Attenuate.
*Surface texture*.—Strigose on both sides.
*Venation*.—Pinnate, with 3 main veins.
*Color*.—Topside Green N137A bottom side Yellow Green 146A.
*Petiole description*.—Grows to 10 cm long and 3 mm wide, strigose, Yellow Green 146A.

Leaf (stem):

*Type*.—Simple.
*Shape*.—Lanceolate.
*Arrangement*.—Alternate.

*Blade size*.—Grows to 12 cm long and 3.4 cm wide.

*Margins*.—Entire to sparsely serrate.

*Apex*.—Acuminate.

*Base*.—Attenuate.

*Surface texture*.—Strigose on both sides.

*Venation*.—Pinnate, with 3 main veins from the base.

*Color*.—Topside Green N137A bottom side Yellow Green 147B.

*Petiole description*.—On lowermost leaves only, clasping, grows to 5 cm long and 4 mm wide above the clasp, glabrous, Yellow Green 147B.

Inflorescence:

*Type*.—Composite on terminal stalked heads.

*Number of flowering stems per plant*.—About 15.

*Flowering stem*.—Grows to 63 cm tall from the base of the plant to the terminal inflorescence and can grow to 21 cm long from the top stem leaf to the base of an inflorescence; branched with 1 to 3 inflorescences per stem; diameter growing to 11 mm wide near the inflorescence; strigose; Yellow Green N144A.

*Size*.—Grows to 11 cm wide and 4 cm deep as disc enlarges.

*Form*.—Ray florets held slightly reflexed, mature disc is conic.

*Immature inflorescence*.—Grows to 4 cm wide and 2.5 cm deep, ray florets held upright and rolled up so only the back color shows, Yellow 18A, disc color Yellow Green 146B.

*Ray florets*.—Without pistil or stamen, ranging from 50 to 80 full size (and 9 to 20 smaller rays growing at irregular angles), grow to 55 mm long and 9 mm wide, oblanceolate with the tip two-toothed (each acute), entire margins, base attenuate, glabrous on both sides; topside Yellow 11A, bottom side Yellow 11B.

*Disc*.—Flat becoming conic, becoming 25 mm deep and 45 mm wide with maturity, Orange 25B.

*Disc florets*.—About 800 in number, each with 1 pistil and 4 stamen, grow to 12 mm long and 1.5 mm wide, each with one persistent, very stiff linear bract (15 mm long with the top 5 mm colored Orange 25B on tip then Yellow Green 144A in middle, then White NN155A on bottom ⅓); corolla 7 mm long and 1.5 mm wide, tubular, 5 lobed, glabrous, Yellow Green 145D except lobes where Yellow Orange 17C; pistil 12 mm long, ovary 5 mm long, White NN155D, style 6 mm long Yellow Green 145C, 2-branched stigma spreading 4 mm wide, Yellow 12A; stamen 8 mm long, filaments 4 mm long and Yellow Green 145D, anthers 3 mm long and Greyed Purple N186A, pollen Yellow Orange 23A.

*Phyllaries*.—In 4 leafy series, area grows to 47 mm wide and 15 mm deep, lobes lanceolate in shape, reflexed, grow to 16 mm long and 3 mm wide, Yellow Green 147B, margins strigose, tip acute, strigose on both sides.

*Receptacle*.—Grows to 20 mm wide and 22 mm deep, White 155B.

*Bloom period*.—July through October in Canby, Oreg.

*Fragrance*.—Good, floral.

*Lastingness*.—Each inflorescence lasts about two weeks in Canby, Oreg.

Seeds: 3 mm long and 2.5 mm wide, oval, Brown 200C.

*Fertility*.—Good.

Disease and pests: *Echinacea* are susceptible to leaf miners, powdery mildew, bacterial spots, and gray mold. None of these have been observed on plants grown under commercial conditions in Canby, Oreg. No resistance is known.

I claim:

1. A new and distinct *Echinacea* plant as herein illustrated and described.

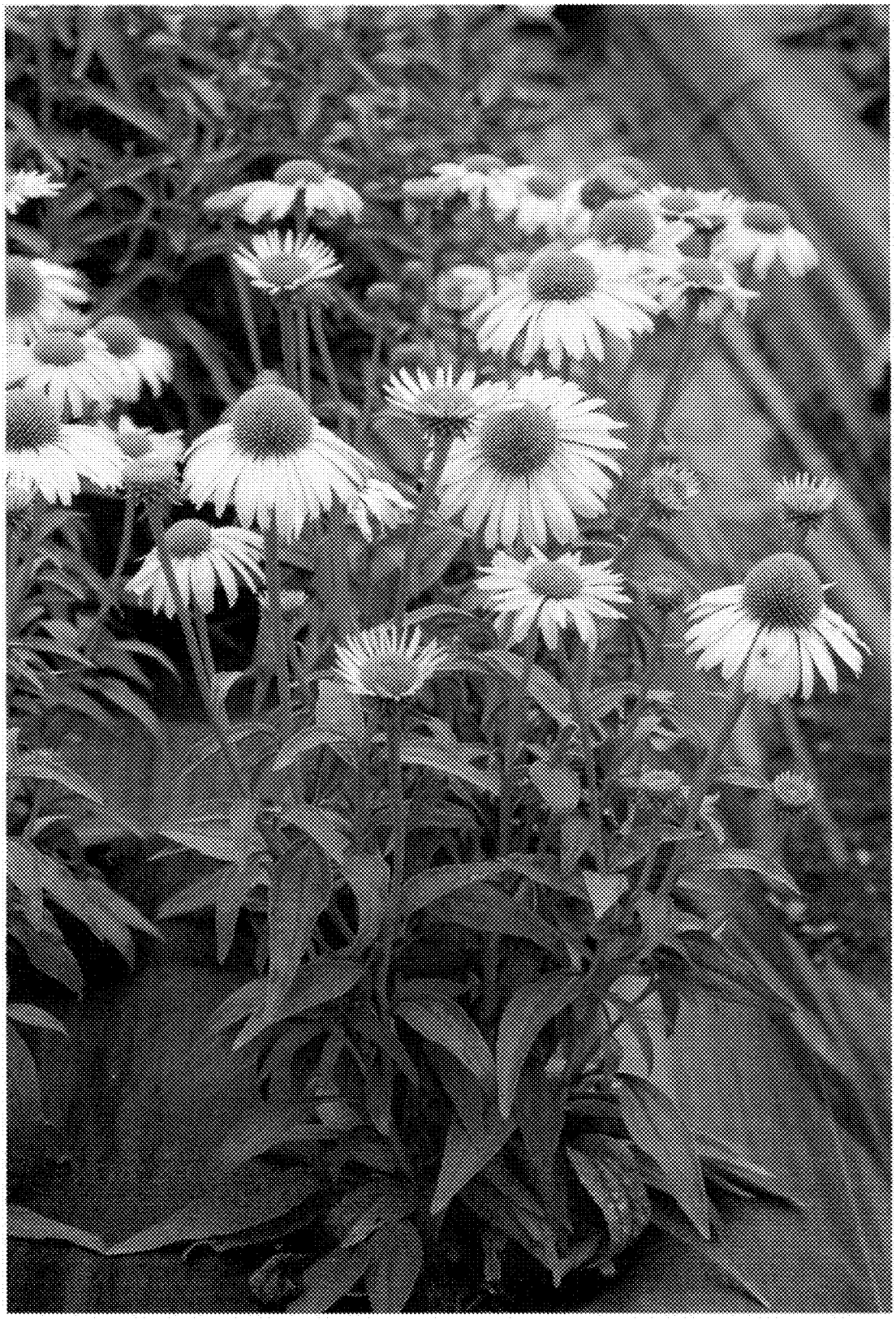

* * * * *